US00PP19940P2

(12) United States Plant Patent
Stervinou

(10) Patent No.: US PP19,940 P2
(45) Date of Patent: Apr. 21, 2009

(54) ***CAMELLIA* PLANT NAMED 'KERGUELEN'**

(50) Latin Name: *Camellia japonica*
Varietal Denomination: Kerguelen

(76) Inventor: Alain Stervinou, Kerguelen, 29290 Guipronvel (FR)

( * ) Notice: Subject to any disclaimer, the term of this patent is extended or adjusted under 35 U.S.C. 154(b) by 0 days.

(21) Appl. No.: 12/152,355

(22) Filed: May 14, 2008

(51) Int. Cl.
*A01H 5/00* (2006.01)

(52) U.S. Cl. ..... Plt./244
(58) Field of Classification Search ..... Plt./244
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of *Camellia japonica* named 'Kerguelen', characterized by its variegated foliage with dark green centers and yellow-green to green-white margins, its broadly upright and compact bushy habit, its thick, leathery, evergreen foliage, its fully double flowers that are light coral pink in color, and its cold hardiness to at least in U.S.D.A. Zone 7.

2 Drawing Sheets

Botanical classification: *Camellia japonica.*
Variety denomination: 'Kerguelen'.

BACKGROUND OF THE INVENTION

The present invention relates to a new and distinct cultivar of *Camellia japonica.* The new cultivar will be referred to hereafter by its cultivar name, 'Kerguelen'. 'Kerguelen' is a suitable for use as a landscape shrub.

The inventor discovered 'Kerguelen' as a naturally occurring branch mutation of *Camellia japonica* 'Nuccio's Cameo' (not patented) in July 1998 and was discovered on a container plant of 'Nuccio's Cameo' at a nursery in Guipronvel, France.

The new cultivar was first asexually propagated by stem cutting by the inventor in August 1998 in Guipronvel, France. It has been determined that the characteristics of this cultivar are stable and are reproduced true to type in successive generations.

SUMMARY OF THE INVENTION

The following traits have been repeatedly observed and represent the characteristics of the new *Camellia* as observed for a period of nine years in Guipronvel, France. These attributes in combination distinguish 'Kerguelen' as a unique cultivar of *Camellia.*

1. 'Kerguelen' exhibits variegated foliage with dark green centers and yellow-green to green-white margins.
2. 'Kerguelen' exhibits a broadly upright and compact bushy habit.
3. 'Kerguelen' exhibits thick, leathery, evergreen foliage.
4. 'Kerguelen' exhibits flowers that are medium to large in size, fully double and formal in form, and light coral pink in color.

The new cultivar of *Camellia* can be readily distinguished from its parent and other cultivars. The parent plant, 'Nuccio's Cameo' lacks variegated foliage. The inventor is not aware of any cultivars of *Camellia japonica* with similar variegation as is observed for 'Kerguelen'. *Camellia*× *williamsii* 'Golden Spangles' has variegated foliage that is dark green with a yellow-green spot in the center of the leaves.

BRIEF DESCRIPTION OF THE DRAWING

The accompanying colored photographs illustrate the overall appearance and distinct characteristics of the new *Camellia,* 'Kerguelen', as grown in Guiponvel, France. The photographs were taken of four year-old plants of 'Kerguelen' as grown in a 3-liter container.

DETAILED BOTANICAL DESCRIPTION

Figure 1:
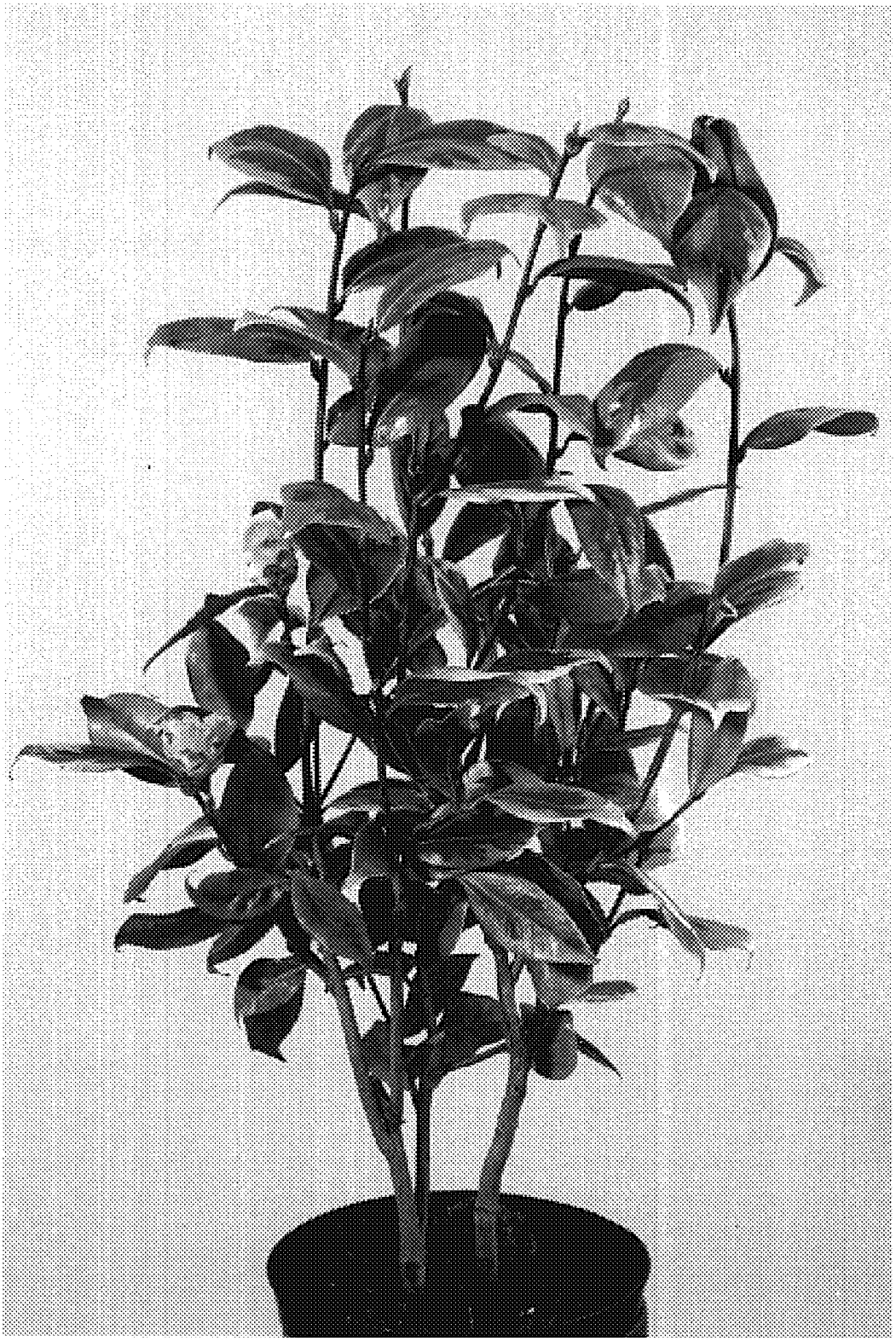
FIG. 1 provides view of the plant habit, FIG. 2 provides a close-up view of a flower, and FIG. 3 provides a close-up view of a mature leaf. The colors in the photographs are as close as possible with digital photography techniques available, the color values cited in the detailed botanical description accurately describe the colors of the new *Camellia.*
Figure 2:
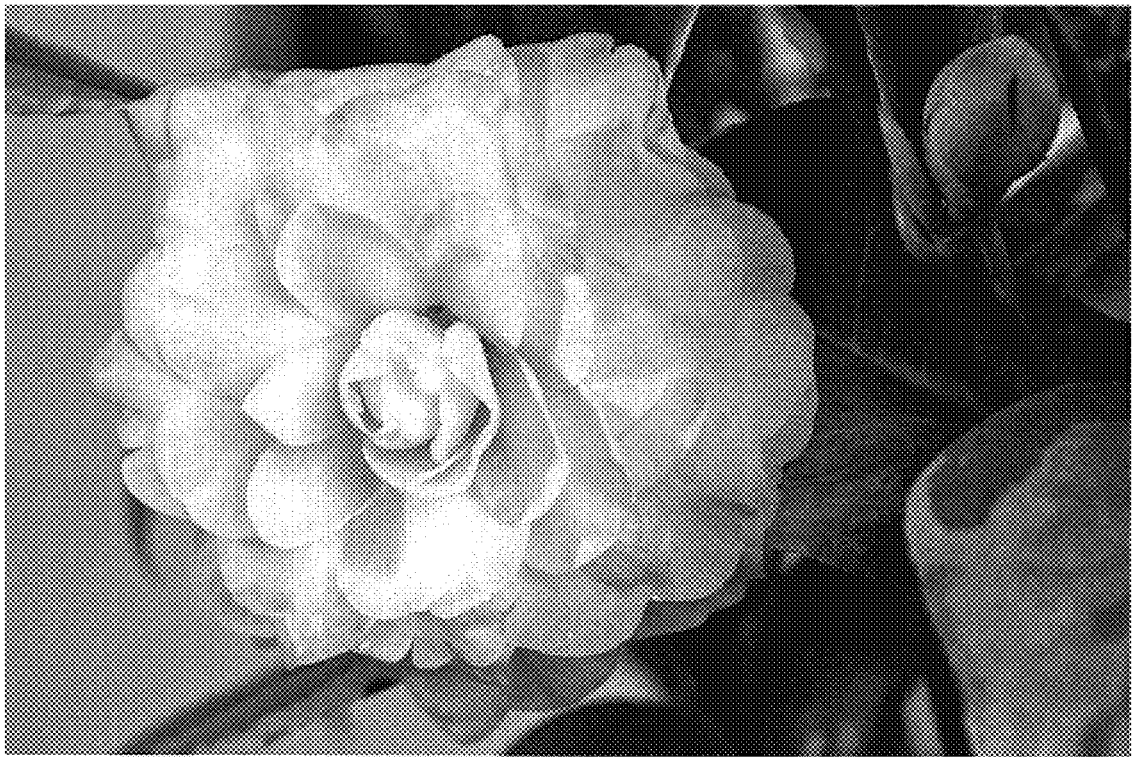
Figure 3:
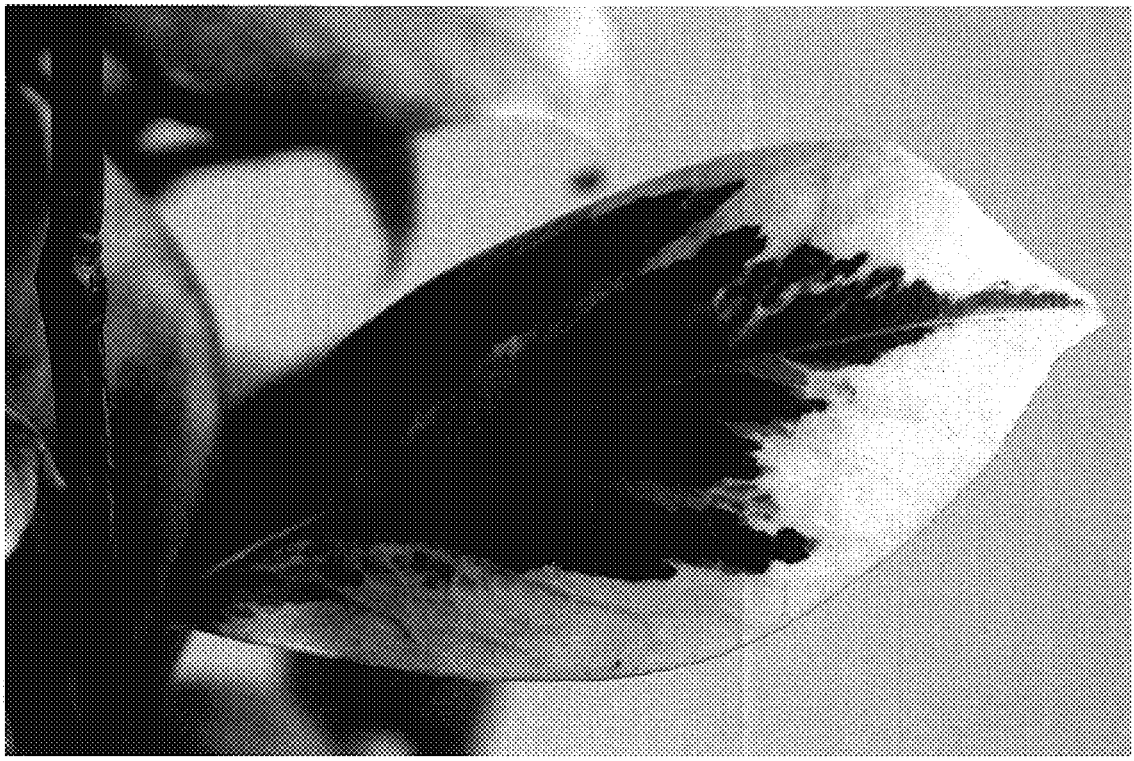

The following is a detailed description of the new cultivar as observed on four year-old plants of 'Kerguelen' as grown in a 3-liter container in Guiponvel, France. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming habit.*—Later winter to early spring (early March to mid April in France).

*Plant habit.*—Evergreen, with a broadly upright and compact bushy habit.

*Height and spread.*—Average of 67 cm in height and 37.8 cm in spread (4 year-old plant).

*Cold hardiness.*—At least to U.S.D.A. Zone 7.

*Heat tolerance.*—At least to temperatures of 35° C.

*Diseases and pests.*—No resistance or susceptibility has been observed.

*Propagation.*—Stem cuttings.

*Growth rate.*—Moderate.

Branch description:

*Stem shape.*—Round.

*Stem strength.*—Strong.

*Stem color.*—Young; 199A flushed with 152A, mature bark; 199B.

*Stem size.*—Average of 20.1 cm in length and 3.5 mm in width.

*Stem surface.*—Young; glabrous, smooth, slightly glossy, adult wood; bark-like, slightly rough to touch.

*Branching.*—Moderately branched with an average of 23 lateral branches.

Foliage description:

*Leaf shape.*—Ovate to elliptic.

*Leaf division.*—Simple.

*Leaf base.*—Rounded to short attenuate.

*Leaf apex.*—Short apiculate.

*Leaf fragrance.*—None.

*Leaf venation.*—Pinnate, color upper lower surface 157A, color lower surface 146B to 146C.

*Leaf margins.*—Serrate.

*Leaf arrangement.*—Alternate.

*Leaf attachment.*—Petiolate.

*Leaf substance.*—Thick and leathery with a high tolerance to stress.

*Leaf surface.*—Smooth and glabrous on upper surface and lower surface, glossy on upper surface.

*Leaf size.*—Average of 9.9 cm in length and 5.1 cm in width.

*Leaf quantity.*—Average of 6 per branch 20 cm in length.

*Leaf variegation pattern.*—Dark green centers surrounded by a yellow-green to green-white colored margins, centers comprise about 50 to 60% of the leaf area, on mature leaves an intermediate color is present blended into centers.

*Leaf color.*—Young leaves upper surface; center 137A to 143A and margin 144B to N144C, young leaves lower surface; 144A to 144B, mature leaves upper surface; center 137A to 137C blushed with 191A to 191B with intermediate area 193A to 193B, and margin 157A to 157B, mature leaves lower surface; center 146B and margin 150C to 150D.

*Petioles.*—Flattened with a width of 3 mm and a height of 2 mm, about 7 mm in length.

*Stipules.*—None.

Inflorescence description:

*Inflorescence type.*—Terminal and axillary solitary, fully double formal flower.

*Flower number.*—Average of 1 per lateral stem.

*Flower fragrance.*—None.

*Flower longevity.*—About 2 weeks, self cleaning.

*Flower type.*—Fully double (lack reproductive organs).

*Flower aspect.*—Outward to slightly upright.

*Flower size.*—Average of 7.4 cm in diameter and 3.4 cm in depth.

*Peduncles.*—Strong, average of 4 mm in length and 2 mm in diameter, surface is glabrous, color is 144A.

*Flower buds.*—Ovate in shape, average of 2.3 cm in length and 1.8 cm in width, color 144B to 144C and 144A near base with apex 65C to 65D and margins of immature sepals 200D, texture is glabrous.

*Sepals.*—10, broadly ovate to broadly obovate in shape, margin is entire, color of upper and lower surface when opening; 144B to 144C and 144A near base, color of upper and lower surface when fully open; 145B with apex base and margin 145C to 145D with 200D near edge of margin, both surfaces are tomentose, average of 1.6 cm in length and 1.4 cm in width, apex is obtuse, base is broadly cuneate, arranged in cup-shaped calyx about 3.2 cm in diameter.

*Petals.*—Average of 6, obovate to obcordate in shape and slightly recurved, upper and lower surface is glabrous and dull, entire margin, cuneate base, obtuse to retuse apex, average of 3.4 cm in length and 2.6 cm in width, color: opening flowers upper surface; 62D with apex 62B to 62C and base N155C, opening flowers lower surface; 62C to 62D with base N155C, fully open flowers upper surface; N155B flushed with a color lighter than 62D, fully open flowers upper and lower surface; between 16B and 16C with inner petals suffused with 22B, color when faded upper and lower surface; N155B.

*Petaloids.*—Average of 70, narrow obovate to narrow obcordate in shape, upper and lower surface glabrous and dull, entire margin, average of 2.5 cm in length and 1.7 cm in width, color upper and lower surface when opening 62D with apex 62B to 62C and base N155C, color upper and lower surface when fully open; N155B flushed with a color lighter than 62D, fading both surfaces; N155B.

*Reproductive organs.*—None.

It is claimed:

1. A new and distinct cultivar of *Camellia* plant named 'Kerguelen' as herein illustrated and described.

* * * * *